(12) United States Patent
Donat et al.

(10) Patent No.: US 10,010,471 B2
(45) Date of Patent: Jul. 3, 2018

(54) COOLING GARMENTS, WARMING GARMENTS, AND RELATED METHODS

(71) Applicant: ISOMER, INC., McLean, VA (US)

(72) Inventors: Terry L. Donat, Sterling, IL (US); David Smith, Falls Church, VA (US)

(73) Assignee: ISOMER, INC., McLean, VA (US)

( * ) Notice: Subject to any disclaimer, the term of this patent is extended or adjusted under 35 U.S.C. 154(b) by 4 days.

(21) Appl. No.: 15/497,953

(22) Filed: Apr. 26, 2017

(65) Prior Publication Data

US 2017/0367917 A1    Dec. 28, 2017

Related U.S. Application Data

(60) Provisional application No. 62/355,771, filed on Jun. 28, 2016.

(51) Int. Cl.
    *A41D 13/005*      (2006.01)
    *A61H 1/00*      (2006.01)
    (Continued)

(52) U.S. Cl.
CPC ............ *A61H 1/008* (2013.01); *A41B 11/005* (2013.01); *A41D 1/002* (2013.01); *A41D 3/08* (2013.01); *A41D 13/0051* (2013.01); *A41D 13/0056* (2013.01); *A41D 13/02* (2013.01); *A41D 19/01* (2013.01); *A41D 19/01535* (2013.01); *A41D 19/01541* (2013.01); *A41D 23/00* (2013.01); *A41D 31/0038* (2013.01); *A42B 1/008* (2013.01); *A42B 1/041* (2013.01); *A42B 1/046* (2013.01); *A42B 1/048* (2013.01); *A43B 3/0005* (2013.01); *A43B 7/005* (2013.01); *A43B 7/02* (2013.01); *A43B 7/34* (2013.01); *A61B 5/0022* (2013.01); *A61B 5/02055* (2013.01);
(Continued)

(58) Field of Classification Search
CPC combination set(s) only.
See application file for complete search history.

(56) References Cited

U.S. PATENT DOCUMENTS 6,473,910 B2    11/2002    Creagan et al.
2007/0204808 A1    9/2007    Harada
(Continued)

OTHER PUBLICATIONS

An International Search Report and the Written Opinion of the International Searching Authority issued by the International Searching Authority dated Aug. 8, 2017 in connection with International Patent Application No. PCT/US2017/029641.

*Primary Examiner* — Joseph Stoklosa
*Assistant Examiner* — Adam Avigan
(74) *Attorney, Agent, or Firm* — Baker & McKenzie LLP

(57) ABSTRACT

The present disclosure generally relates to intelligent garments that provide thermal regulation in a variety of environments. The garments may include different layers such as a hydrophilic layer in direct contact with a wearer's skin surface and saturated with an aqueous mixture, a spacer layer, a reflective layer, and an outer hydrophobic layer. The layers of the garment may work together to reduce the metabolic expenditure of the wearer in extreme environmental conditions or during demanding physical activity. A variety of sensors may be displaced throughout the garments so as to enable the collection of data associated with wearers as well as environmental conditions. Wearers may control the thermal balance and other properties of the garments as desired.

21 Claims, 12 Drawing Sheets

(51) Int. Cl.

| | | |
|---|---|---|
| *A41B 11/00* | (2006.01) | |
| *A41D 1/00* | (2018.01) | |
| *A41D 3/08* | (2006.01) | |
| *A41D 13/02* | (2006.01) | |
| *A41D 19/01* | (2006.01) | |
| *A41D 19/015* | (2006.01) | |
| *A41D 23/00* | (2006.01) | |
| *A41D 31/00* | (2006.01) | |
| *A42B 1/04* | (2006.01) | |
| *A43B 3/00* | (2006.01) | |
| *A43B 7/00* | (2006.01) | |
| *A43B 7/02* | (2006.01) | |
| *A43B 7/34* | (2006.01) | |
| *A61B 5/0205* | (2006.01) | |
| *A61F 5/37* | (2006.01) | |
| *A61F 7/02* | (2006.01) | |
| *H04Q 9/00* | (2006.01) | |
| *A42B 1/00* | (2006.01) | |
| *A61B 5/00* | (2006.01) | |
| *A61B 5/021* | (2006.01) | |
| *A61B 5/024* | (2006.01) | |
| *A61B 5/11* | (2006.01) | |

(52) U.S. Cl.
CPC .......... *A61B 5/6804* (2013.01); *A61F 5/3738* (2013.01); *A61F 7/02* (2013.01); *H04Q 9/00* (2013.01); *A41D 2023/002* (2013.01); *A41D 2400/22* (2013.01); *A61B 5/021* (2013.01); *A61B 5/02438* (2013.01); *A61B 5/11* (2013.01); *A61B 2560/0242* (2013.01); *A61F 2007/0234* (2013.01); *A61F 2007/0236* (2013.01); *A61F 2007/0266* (2013.01); *A61H 2201/0207* (2013.01); *A61H 2201/0214* (2013.01); *H04Q 2209/10* (2013.01)

(56) References Cited

U.S. PATENT DOCUMENTS

| | | |
|---|---|---|
| 2008/0040839 A1 | 2/2008 | Gordon |
| 2009/0313748 A1* | 12/2009 | Guedes Lopes Da Fonseca .................. G06F 1/163 2/458 |
| 2012/0157904 A1* | 6/2012 | Stein ........................ A61F 7/02 602/43 |
| 2012/0190259 A1 | 7/2012 | Frost |
| 2015/0374045 A1 | 12/2015 | Codner et al. |

* cited by examiner

COOLING GARMENTS, WARMING GARMENTS, AND RELATED METHODS

CROSS-REFERENCE TO RELATED APPLICATIONS

The present application is a utility application of, and claims priority to, U.S. Provisional Application No. 62/355,771 filed on Jun. 28, 2016, the entirety of which is incorporated by reference.

BACKGROUND

The human body is quite efficient at regulating body temperature. However, in extreme environmental conditions or during extreme physical exertion, the human body may be unable to regulate body temperature in a manner that is required for maintaining a desired level of health or a desired level of physical performance. For example, a professional athlete competing at a maximum level of physical exertion and in extremely hot and humid conditions may be at risk of experiencing a heat stroke. As another example, in extremely cold weather conditions, a person's body may struggle to maintain a healthy core body temperature, and as a result the person may be exposed to risks associated with hypothermia. Thus, garments for regulating body temperature more efficiently so as to reduce metabolic strain on the body, particularly in extreme conditions, are desired.

BRIEF SUMMARY

The present disclosure generally relates to intelligent garments for enhancing body heat transfer from a skin surface of a wearer into surrounding atmospheric environments while concurrently reducing physiological, metabolic, and neuropsychological expenditures. The garments described herein may be utilized in extreme conditions such as high environmental and micro-environmental temperatures, low environmental and micro-environmental temperatures, saturating humidity levels, submersion or exposure to low-temperature water or low atmospheric temperature levels, high levels of environmental thermal irradiation, low levels of environmental thermal irradiation, body tissue discomfort or injury, and extreme psychological stress.

As a result, the garments described herein may reduce the amount of metabolic resources required for maintaining a desired body temperature. For example, the garments described herein may reduce a wearer's need to sweat when cooling off, or conversely reduce an amount of expenditure required for keeping a wearer warm. The garments disclosed herein involve operational use of the garments as well as use of embedded, worn, and networked sensor arrays to predict, monitor, survey, adapt, and optimize performance of garments and wearers.

In some embodiments, the garments described herein may be applicable to a variety of types of users, including: the young, the debilitated, and the elderly; those with functionally-reduced body surface such as amputees and recovered burn victims; those who suffer acute or chronic soft-tissue inflammation as a result of sun-exposure, hypersensitivity reactions, disease, superficial first- and second-degree burns, trauma, overexertion, and surgery; those who experience dysfunction of central thermoregulatory centers or peripheral responses as a consequence of menopause, malignant hyperthermia, medication or drug side-effects and central nervous system injury; those without access or who unexpectedly or emergently lose access to cooling homes, transportation, and other inhabited spaces reliant upon residential or commercial power during power outages, adverse weather, evacuation or disaster; persons at commonplace voluntary risk due to ambient environmental heat exposure such as outdoor construction and roofing workers, maritime, longshore, and shipbuilding workers, agricultural workers, mining and oil/gas industry workers, landscaping and outdoor maintenance personnel, warehousing workers, chefs, cooks, kitchen workers, outdoor recreational workers, athletes, and outdoor event spectators; persons who engage in exceptional voluntary risk with occupational duties and obligations to don protective apparel (e.g., a personal protective ensemble (PPE) which protects them from one or more life-threatening hazards but which severely limits body heat loss by creating a thermal barrier with a perspiration-saturated microclimate beneath the PPE) such as healthcare workers, law enforcement, search and rescue personnel, special weapons and tactics personnel, firefighters, explosive ordnance disposal personnel, hazardous materials technicians, training, armed conflict, and supportive logistical military personnel, working dogs, electrical, utility, public works, and welding/fabrication workers, roadway, railway, shipping, flight crews, aeronautical construction and maintenance personnel, and athletes in thermally or physically protective apparel (e.g., high-performance motor sports, football, ice hockey, and/or the like). The garments may also be adapted for use with animals such as pets, civilian and military working dogs, zoo animals, tournament and sport animals, and exhibition animals.

BRIEF DESCRIPTION OF THE DRAWINGS

Reference is now made to the following descriptions taken in conjunction with the accompanying drawings.

DETAILED DESCRIPTION

Various embodiments of garments are described according to the present disclosure. It is to be understood, however, that the following explanation is merely exemplary in describing the devices and methods of the present disclosure. Accordingly, several modifications, changes, and substitutions are contemplated.

Figure 1:
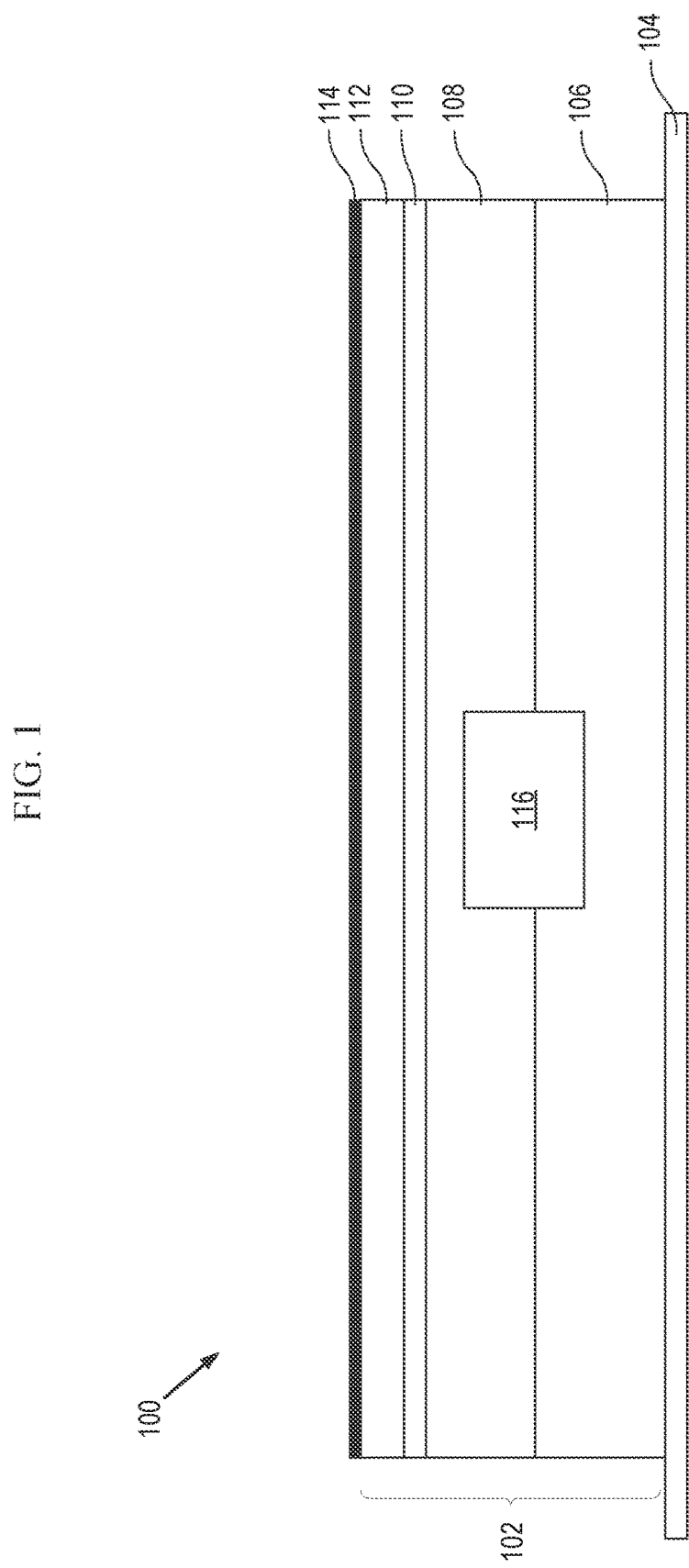
FIG. 1 illustrates an exemplary cross-sectional view of garment layer construction according to the present disclosure.

FIG. 1 illustrates an exemplary cross-sectional view of a layer construction 100 of a garment 102. The garment 102 may generally be a contact-fitted garment or undergarment. In some embodiments, the garment 102 may be worn beneath street clothes, PPE, a uniform, or outerwear. Alternatively, the garment 102 may include fitted outerwear, hooded, draped, wrapped, and/or otherwise covering apparel. The garment 102 may also include seating, matting, bedding, blanketing, and/or enveloping shrouds.

The garment 102 may be disposed (e.g., worn) on an outer skin surface 104 of a wearer. By being in direct contact with the skin surface 104, the garment 102 may be enabled to regulate the cooling, heating, buffering, and/or maintenance of the wearer's body temperature in an efficient manner. Additionally, when worn, the garment 102 may be positioned on the skin surface 104 so as to maximize the surface area of the skin surface 104 in direct contact with the garment 102. This may ensure accurate monitoring and control of heat transfer away from and/or toward the skin surface 104.

The garment 102 may be constructed as a single continuous garment portion. Alternatively, the garment 102 may be constructed as multiple garment portions. Multiple garment portions may be coupled together via seams, zippers, buttons, clasps, welds, stitches, clamps, adhesives, and/or other couplings. For example, a first garment portion may cover a first body portion of the wearer, whereas a second garment portion adjacently coupled to the first garment portion may cover a second body portion. The garment 102 may be positioned over any external non-mucosal skin surface 104 of the wearer's body.

In some embodiments, the layer construction 100 of the garment 102 may be approximately ¼-inch thick. In other embodiments, the layer construction 100 of the garment 102 may be thicker, particularly for medical applications where extra padding and/or support is required.

In some embodiments, the garment 102 may include a basal layer 106 in direct contact with the skin surface 104. The basal layer 106 may include a hydrophilic material capable of fluid adsorption. With respect to materials, the basal layer 106 may be manufactured from a woven fabric, a nonwoven fabric or porous matrix (e.g., sponge) of hydrophilic material, and/or the like. For example, the basal layer 106 may include animal wools, cellulosic fibers such as cotton, bamboo, hemp, soy, silk, and/or other natural fiber derivatives, semisynthetic fibers such as rayon, modal, lyocell, and synthetic fabrics such as polyester, acrylonitrile, polylactide, polyethylene polypropylene, and activated carbon fiber fabric, and/or natural and synthetic sponge materials.

As described herein, a liquid or other fluids may be adsorbed to the basal layer 106 so as to achieve desired cooling and/or warming effects. A fluid-adsorbed basal layer 106 may provide surrogate evaporation for heat exchange to the environment (e.g., outside of the garment 102) despite extreme environmental temperatures, water vapor saturation levels, and/or dew points. Additionally, the basal layer 106 may provide conductive and/or radiative means for heat transfer from the skin surface 104 into an adsorbed liquid of the basal layer 106. In this manner, the basal layer 106, may enable production and/or retention of an aqueous heat sink within the basal layer 106 of the garment 102.

The liquid adsorbed into the basal layer 106 may include an aqueous, thermodynamic liquid. For example, the liquid may include a variety of fluids such as water, alcohols, and/or an aqueous mixture of the same. Exemplary alcohols include ethanol, propanol, and isopropanol. Other primary or secondary alcohols may be utilized as well. In some embodiments, a total initial volatile alcohol component composition is at least approximately 5% and no more than approximately 50% by volume.

Prior to being worn, the liquid may be adsorbed to the basal layer 106 via surface fiber adsorption, core fiber imbibition, soaking, wetting, submersion, electrostatic deposition, saturation, perfusion, injection, and/or the like. A predetermined amount of liquid may be desired for adsorption in the basal layer 106 of each garment design. During operation and/or over time, the liquid adsorbed into the basal layer 106 may spontaneously deplete. For example, the liquid may evaporate, be absorbed by the skin surface 104, seep out of the garment 102, and/or the like. As such, the liquid may need to be replenished. In some embodiments, replenishing the liquid in the basal layer 106 may include replacement, re-submersion, re-wetting, re-perfusion, re-injection, and/or the like. The replacement liquid may be obtained from a reservoir internal to and/or external to the garment 102.

As seen in FIG. 1, the garment 102 may further include a spacer layer 108 positioned (e.g., displaced and/or superimposed) on top of and in direct contact with an outer surface of the basal layer 106. The spacer layer 108 may enable evaporative and/or convective loss of the liquid of the basal layer 106. For example, the spacer layer 108 may include one or more vents for enabling a volatile component of the liquid of the basal layer 106 (e.g., an alcohol component) to evaporate and thus transfer heat from the skin surface 104 to the outside ambient environment. By being highly permeable to vapor and/or water, the spacer layer 108 may serve as a conductive and/or convective barrier to prevent the transfer of heat from the outside ambient environment to the skin surface 104.

The spacer layer 108 may be manufactured from a rigid and/or non-rigid material. For example, the spacer layer 108 may include three-dimensional and/or four-dimensional fabric meshes, discrete micro-molded polymer spacers, pleating, piping, inserts, tubing, corrugations, bolsters, buttresses, open-cell foam, and/or other warp-knitting or stretchable woven materials. In some embodiments, the thickness of the spacer layer 108 may be within a range of approximately 6 millimeters thick to approximately 10 millimeters thick.

The garment 102 may further include a reflective layer 110 positioned (e.g., displaced and/or superimposed) on top of and in direct contact with an outer surface of the spacer layer 108. The reflective layer 110 may include a thermal radiant-reflective and/or thermal radiant-modulating material that functions to efficiently regulate cooling and/or warming effects upon the skin surface 104. For example, the reflective layer 110 may reflect heat being emitted from the skin surface 104 in efforts to keep the skin surface 104 warm. Alternatively, the reflective layer 110 may be operated in such a way as to prevent heat emitted from the environment from passing into the layers 106 and 108 or reaching the skin surface 104. For example, the reflective layer 110 may include one or more closeable holes.

The reflective layer 110 may include infrared radiant-reflective and/or radiant-modulating materials such as sealed or unsealed multilayer metallized (e.g., metal or metallic) aluminum, gold, silver and other metallized foils, metallized films, metallized fabrics, metallized coatings, metallized laminations, metallized composite fabrics, and/or metallized aerogels. The reflective layer 110 may be used to control and/or adjust the water and/or vapor permeability of the garment 102.

The garment 102 may further include a hydrophobic layer 112 positioned (e.g., displaced and/or superimposed) on top of and in direct contact with an outer surface of the reflective layer 110. The hydrophobic layer 112 may allow for one-way or two-way escape of vapor and/or moisture emitted from the skin surface 104 to the ambient environment. The hydrophobic layer 112 may also act as a seal that disallows any transfer of vapor or moisture from the ambient environment to the remainder of the garment and/or the skin surface 104. In some embodiments, the hydrophobic layer 112 may be treated with waterproofing and may also be reversible.

The garment 102 may further include a compression layer 114. The compression layer 114 may serve as a superficial layer composed of a fabric with compression properties and/or effects for ensuring that the garment 102 maintains contact with the underlying skin surface 104. One or more of the other layers of the garment 102 (e.g., the basal layer 106, the spacer layer 108, the reflective layer 110, and/or the hydrophobic layer 112) may include compression materials as well. In other embodiments, the garment 102 may not include the compression layer 114.

One or more of the basal layer 106, the spacer layer 108, the reflective layer 110, the hydrophobic layer 112, and/or the compression layer 114 may include treated functionality such as water-resistance, water-proofing, chemical-proofing, flame-retardation, electrical grounding, magnetic degaussing, and/or the like. This treated functionality may integrated into the garment 102 without interference in operation as described herein. Each of the layers 106, 108, 110, 112, and/or 114 may include compression materials, composite materials, and/or synthetic materials. One or more of the layers 106, 108, 110, 112, and/or 114 may be bonded to each other via sewn stitches, needle punching, lamination, quilting, bonding agents, adhesives, clasps, clamps, buttons, snaps, and/or other couplings.

The layer construction 100 of the garment 102 can be utilized for providing both cooling and warming effects. For example, in some embodiments, the liquid infused with the basal layer 106 may be a warm liquid such that the wearer of the garment 102 maintains warmth when the garment is worn in cold conditions. Additionally, when the garment 102 is worn in cold conditions, the outermost hydrophobic layer 112 may be sealed in both directions so that vapor and/or moisture do not pass either from the skin surface 104 to the ambient environment or from the ambient environment to the skin surface 104 Alternatively, the liquid infused with the basal layer 106 may be a cool liquid such that the wearer of the garment 102 is cooled when the garment is worn in warm conditions. Additionally, when the garment 102 is worn in warm conditions, the outermost hydrophobic layer 112 may be opened (e.g., vented) in both directions so that vapor and/or moisture may pass therethrough (e.g., either from the skin surface 104 to the ambient environment and/or from the ambient environment to the skin surface 104).

Also shown in the layer construction 100 of the garment 102 of FIG. 1 is a sensor 116. One or more sensors (e.g., sensor 116) may be displaced within and/or otherwise embedded into the layer construction 100 of the garment 102 in various locations. The sensor 116 may include multiple sensors.

In some embodiments, the sensor 116 may measure biophysiological values of the wearer and/or characteristics of the garment 102 and/or individual garment layers. For example, the sensor 116 may collect information associated with the wearer such as a skin surface temperature, a heart rate, a breathing rate, a skin surface conductivity, and/or other information associated with the wearer. The sensor 116 may also collect information associated with the garment 102 such as a sensor position, a motion of the sensor, a liquid level, a humidity level, a moisture level, a thickness, a weight, a tensile strength, and/or the like. The sensor 116 may also collect information associated with the environment external to the garment 102 such as ambient condition values of air temperature, air humidity, wind speed, dry or dry bulb temperatures, air pressure, altitude, infrared, optical, and UV irradiance, and/or the like.

The sensor 116 may include a variety of input/output (I/O) devices as described herein such as a probe, an actuator, an accelerometer, a monitor, and/or the like. As described in more detail below, the sensor 116 may embody one or more elements of the computing environment 1100 shown in FIG. 11 and FIG. 12.

The sensor 116 may collect data at predetermined sampling intervals and/or substantially in real time. In some embodiments, the sensor 116 may transmit collected data to a data center (e.g., data center 1006 of FIG. 10) and/or another central data repository for storage and/or processing. The sensor 116 may also transmit collected data to a user device of the wearer for controlling the functionality of the garment 102. Data collected by the sensor 116 may be transmitted by the sensor 116 substantially simultaneously to collecting the data, at predetermined intervals, upon connection to a predetermined network and/or a predetermined device, and/or the like.

The data center may receive the data collected by the sensor 116 of the garment 102 as well as data collected from other sensors of the same garment 102 and/or other sensors associated with other garments. In this manner, the data center may aggregate information associated with a variety of garments, users, wearers, environments, and/or the like.

The data center may allow one or more users to access this aggregated information. For example, a wearer of the garment 102 may be enabled to access data associated with the garment 102, the wearer, and/or environmental conditions via a user device (e.g., smart phone, wearable device, and/or the like). The wearer of the garment 102 may use the user device, which is in communication with the data center, to control operation of the garment 102. For example, the wearer may determine, based on the data associated with the garment 102 presented to the wearer via the user device, that environmental conditions are extremely cold. In response, the wearer may adjust one or more settings of the garment 102 and/or garment layers 106, 108, 110, 112, 114 for a duration of time so that less heat is transferred outside of the garment 102 and more heat is reflected inward toward the skin surface 104. In this manner, the wearer may buffer himself/herself from disadvantageous measures of thermal balance through time (e.g., minutes, hours, days, weeks, months, and/or years) in harsh environments. Additionally, the wearer of the garment 102 may achieve advantageous in-activity cooling, in-activity warming, pre-cooling, pre-warming, post-cooling, post-warming, interactivity cooling, and/or interactivity warming as desired.

Further, a user associated with a management center (e.g., management center 1008 of FIG. 10) may be enabled to access this information. A management center may include a variety of entities such as a hospital, a research laboratory, a product design company, a medical facility, a field medical response team, a resource support team, an IT facility, and/or another institution. For example, a garment manufacturer may access the data stored at the data center via a computing device terminal (e.g., a laptop, a desktop, a tablet, a smart phone, and/or the like) and used the data collected by the sensor 116 to identify design modifications and improvements to be made to the garment 102.

In some embodiments, the data collected and aggregated by the data center may be used by the management center to continuously monitor environmental conditions, continuously monitor wearer behavior and/or vitals (e.g., health and/or medical information), identify trends among garment wearers, and/or the like. Ambient environment information may be analyzed along with past, present, and/or predicted future data associated with the garment 102 and/or the wearer. Based on analyzing this aggregated sensor data, the management center may alert emergency response personnel in the event that a wearer's vitals show that the wearer is at risk. As another example, the management center may be enabled to control the functionality of the garment 102 to make the wearer more comfortable, achieve higher levels of performance, and/or otherwise provide situational awareness to the wearer over time. Various reports may also be generated by the management center.

In some embodiments, information included in the data center and/or information used by the wearer and/or management center may include weather information such as current weather conditions, historical weather conditions, and/or forecast weather conditions, environmental indoor and/or outdoor air quality data, solar infrared, ultraviolet, and/or visible irradiance data, altitude and/or variation data, geospatial location integration data, and/or the like. The information included in the data center and/or information used by the wearer and/or management center may also include information collected by the sensor 116 as well as information collected by other sensors at various points in time. The collected data in the data center may be sorted, filtered, analyzed, processed, displayed, and/or otherwise manipulated in a variety of ways so as to be productively utilized by the management center and/or the wearer.

Figure 2:
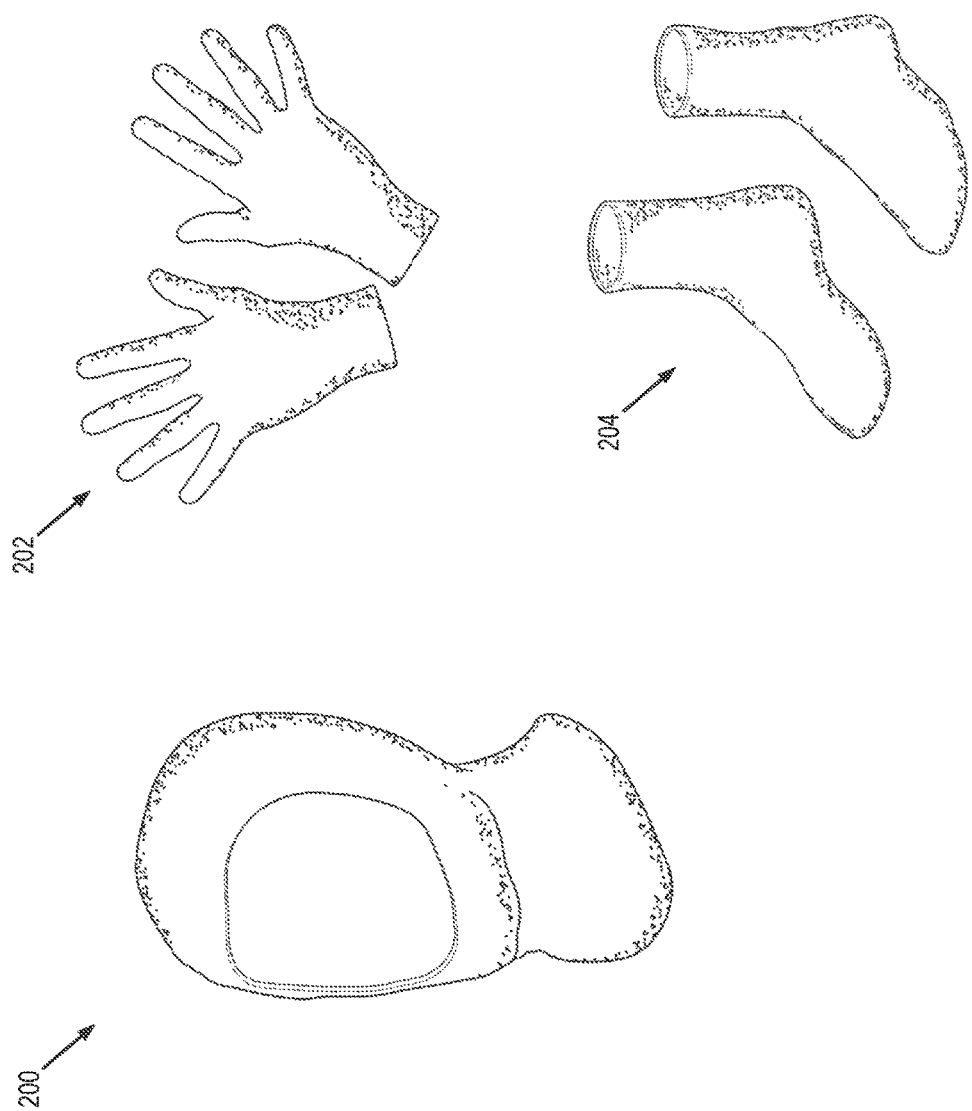
FIG. 2 illustrates exemplary perspective views of a hood, gloves, and boots according to the present disclosure.

As seen in FIG. 2, the garment may include a facemask 200 (e.g., a hood, a hat, a balaclava, a toboggan, and/or the like), gloves 202 (e.g., mittens and/or the like), and/or boots 204 (e.g., socks, shoes, sandals, and/or the like). In some embodiments, the facemask 200 may entirely cover a wearer's face. In some embodiments, the boots 204 may include rubber and/or composite soles for traction.

Figure 3:
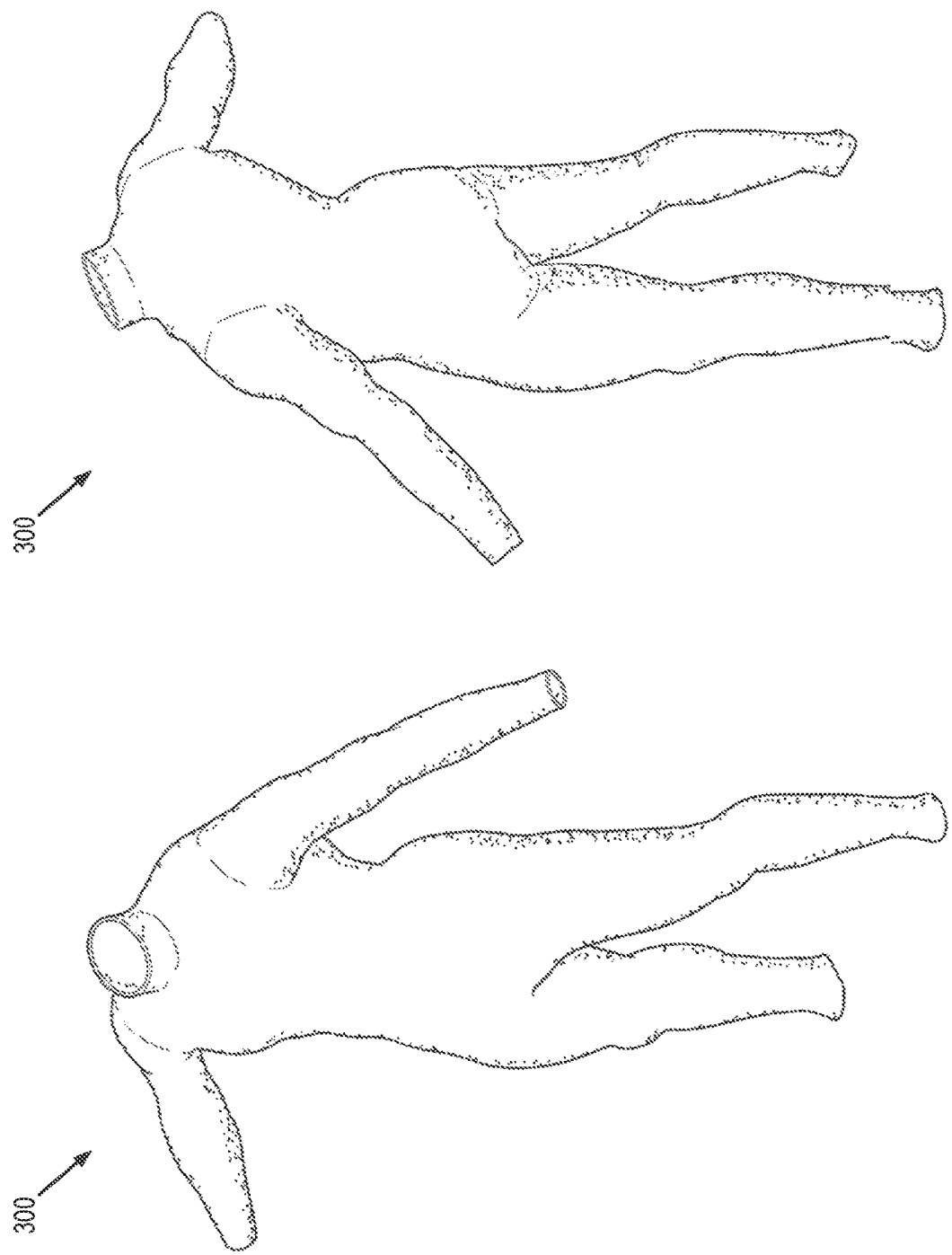
FIG. 3 illustrates exemplary front and rear perspective views of a full-body ensemble according to the present disclosure.

As seen in FIG. 3, the garment may include a full-body ensemble 300 (e.g., a jumpsuit, a skeleton suit, a flight suit, and/or the like). In some embodiments, the full-body ensemble 300 may be manufactured from one or more adjacently-coupled garment portions so as to substantially cover the entirety of a wearer's body.

Figure 4:
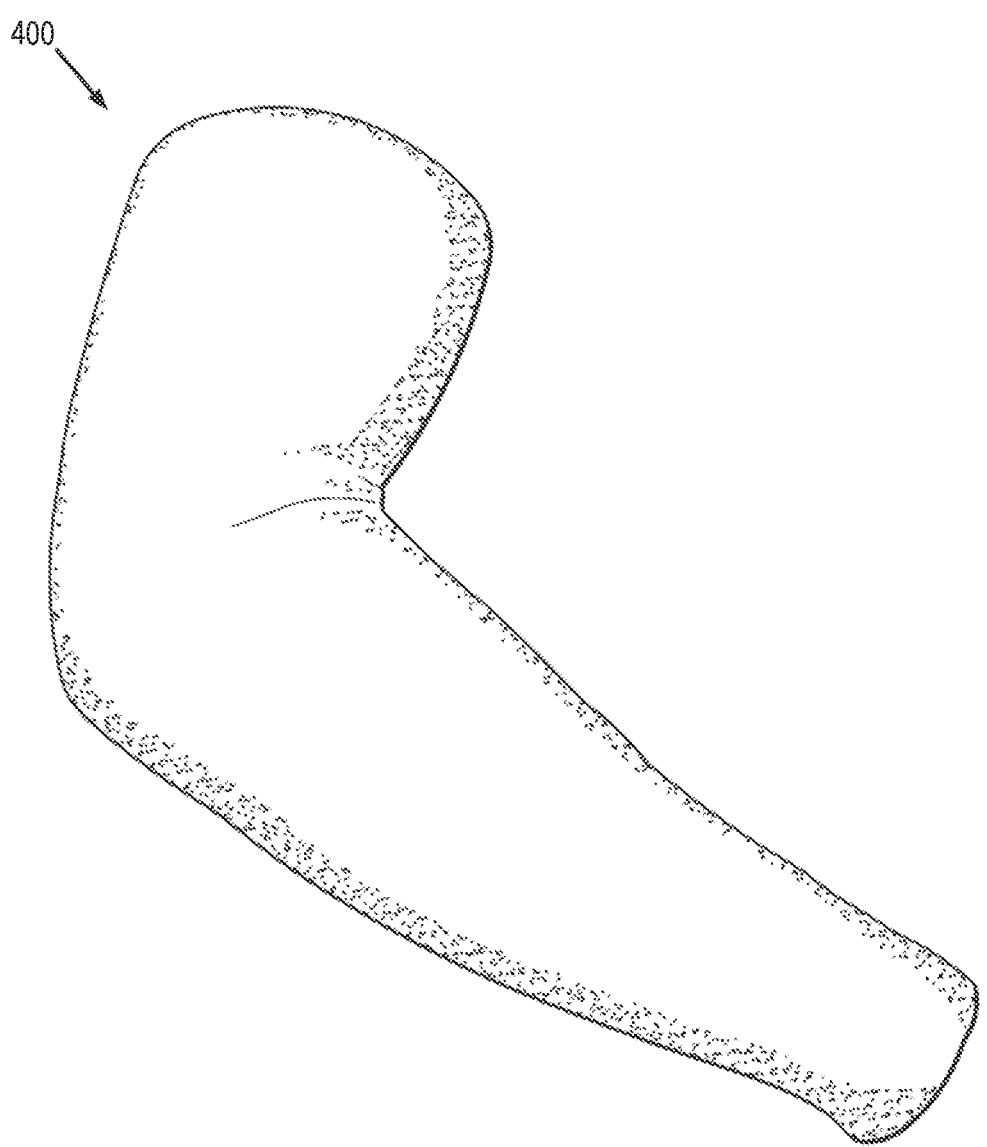
FIG. 4 illustrates an exemplary perspective view of an arm sleeve according to the present disclosure.

As seen in FIG. 4, the garment may include an arm sleeve 400 (e.g., a compression sleeve, an orthopedic or orthotic sleeve, an elbow sleeve, an upper arm sleeve, a forearm sleeve, a wrist sleeve, and/or the like). The arm sleeve 400 may include an arm hole through which a wearer may insert his or her arm when putting on the arm sleeve 400.

Figure 5:
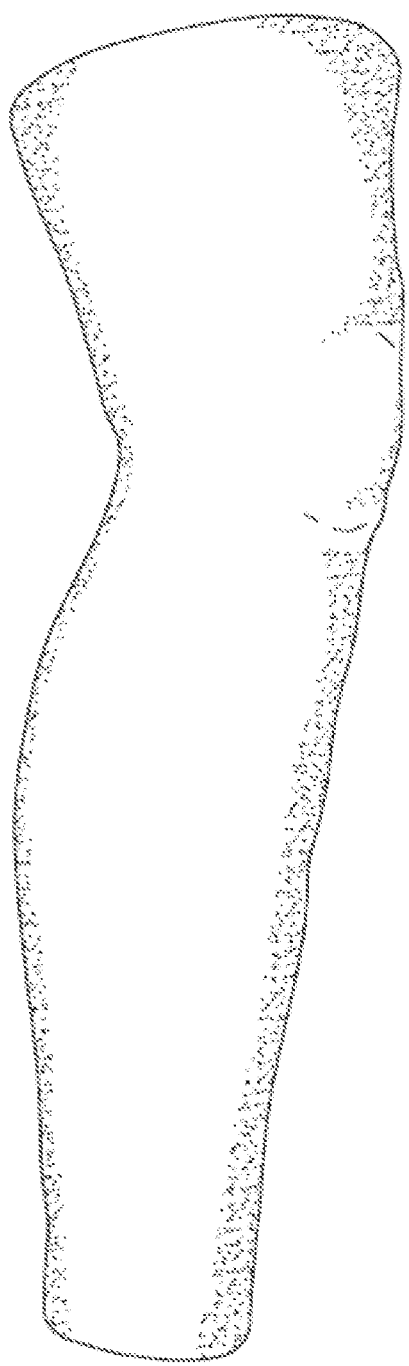
FIG. 5 illustrates an exemplary perspective view of a leg sleeve according to the present disclosure.

As seen in FIG. 5, the garment may include a leg sleeve 500 (e.g., a compression sleeve, an orthopedic or orthotic sleeve, a knee sleeve, a thigh sleeve, a shin sleeve, an ankle sleeve, and/or the like). The leg sleeve 500 may include an arm hole through which a wearer may insert his or her leg when putting on the leg sleeve 500.

Figure 6:
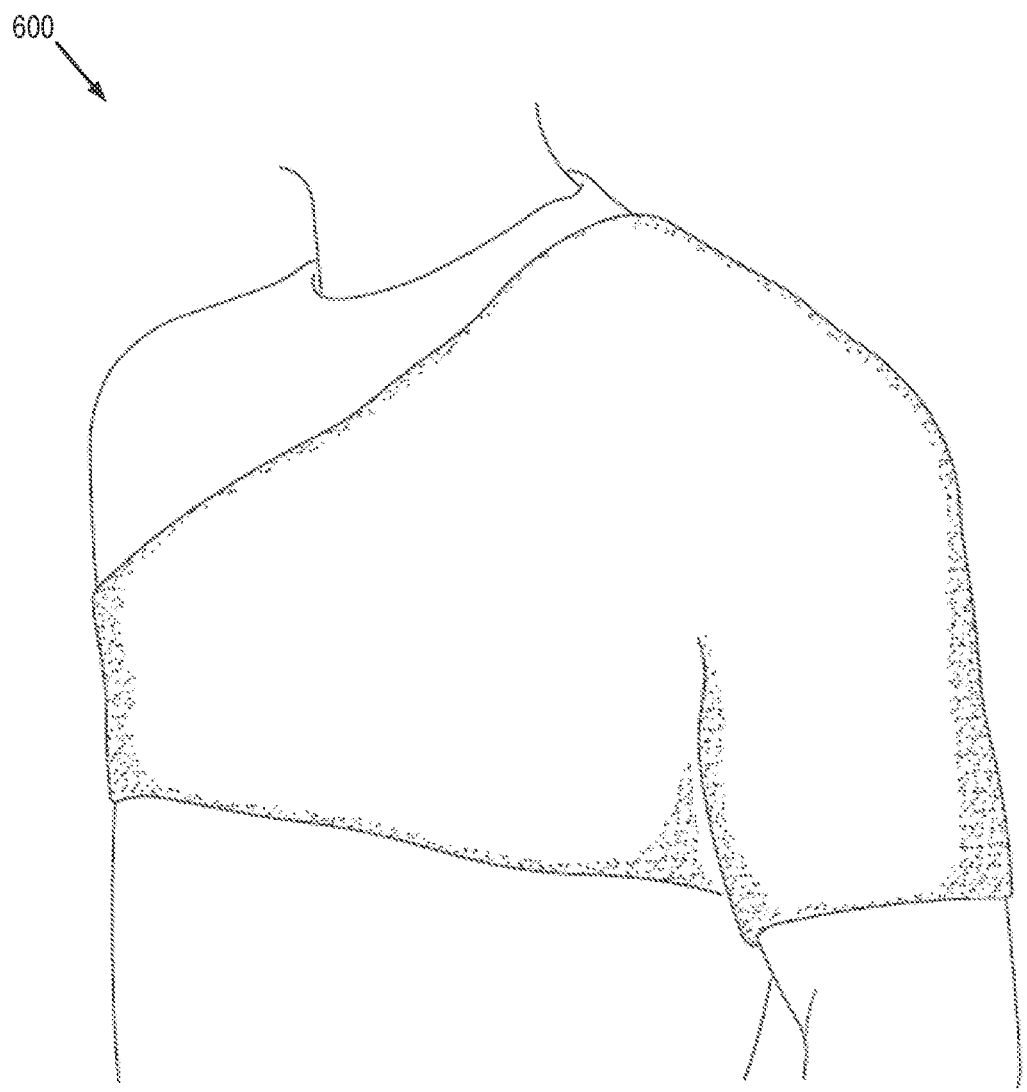
FIG. 6 illustrates an exemplary perspective view of a shoulder support according to the present disclosure.

As seen in FIG. 6, the garment may include a shoulder sleeve 600 (e.g., a compression sleeve, an shoulder support, a sling, and/or the like). The shoulder sleeve 600 may include an arm hole through which a wearer may insert his or her arm when putting on the shoulder sleeve 600. The shoulder sleeve 600 may also include a torso hole through which a wearer may insert his or her torso when putting on the shoulder sleeve 600.

Figure 7:
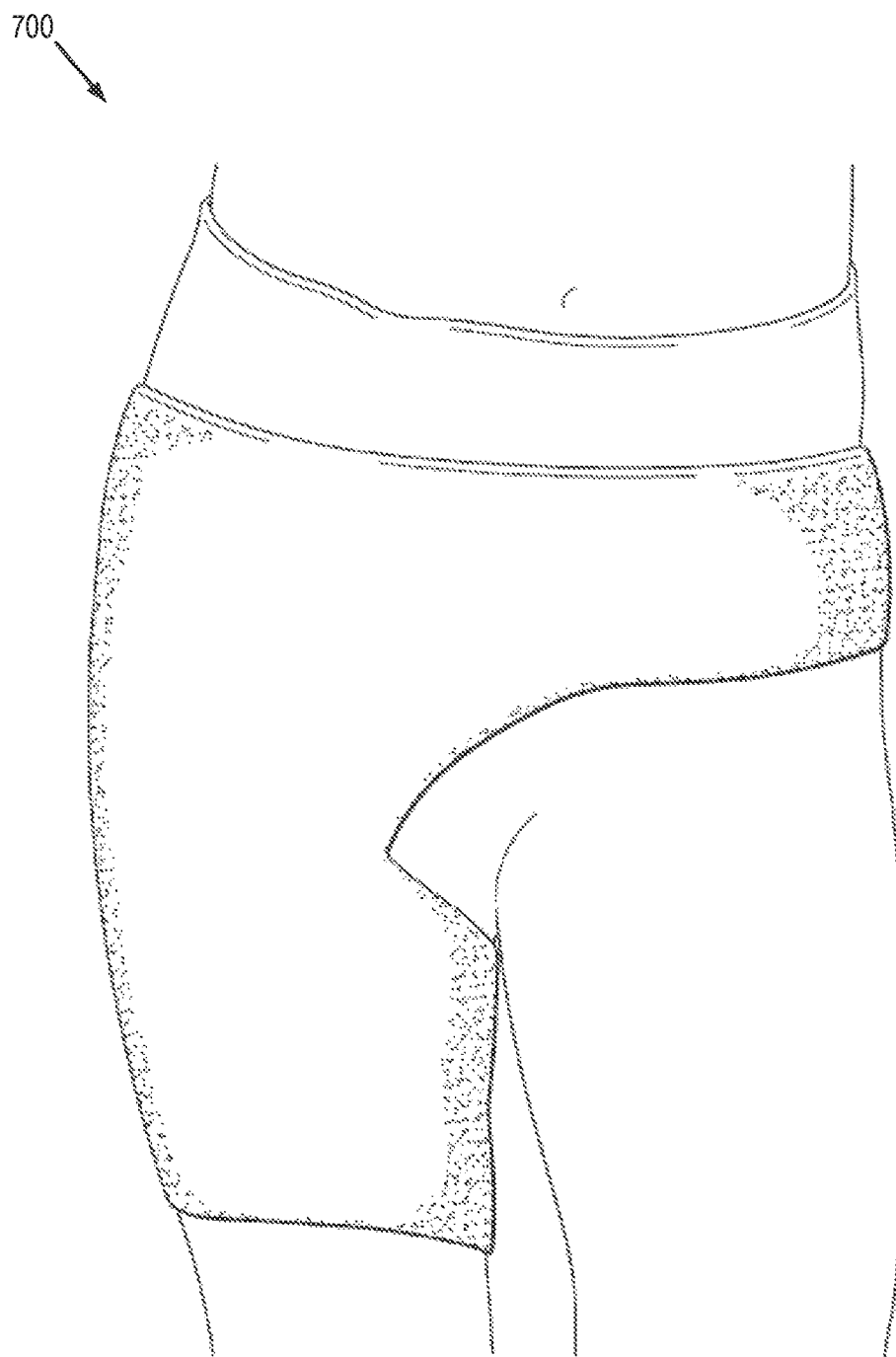
FIG. 7 illustrates an exemplary perspective view of a hip support according to the present disclosure.

As seen in FIG. 7, the garment may include a hip sleeve 700 (e.g., a compression sleeve, an hip support, a sling, and/or the like). The hip sleeve 700 may include a leg hole through which a wearer may insert his or her leg when putting on the hip sleeve 700. The hip sleeve 700 may also include a torso hole through which a wearer may insert his or her torso when putting on the hip sleeve 700.

Figure 8:
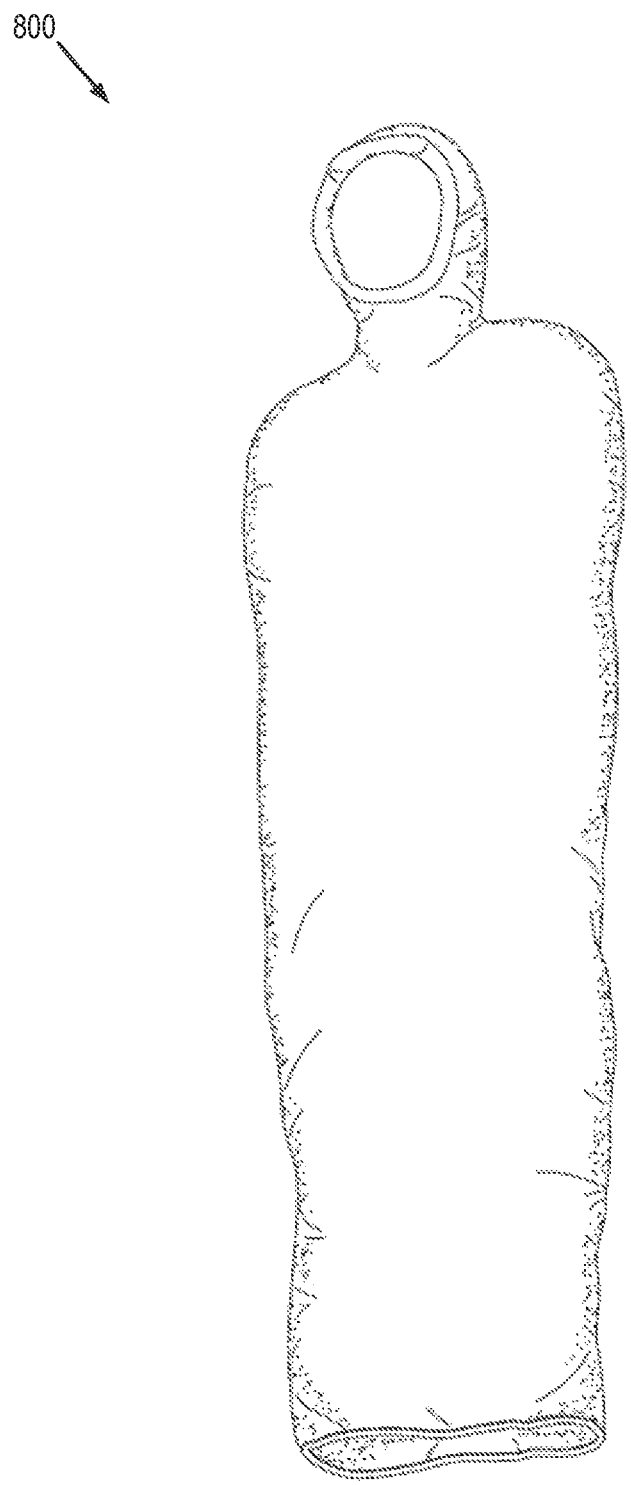
FIG. 8 illustrates an exemplary perspective view of a blanket according to the present disclosure.

As seen in FIG. 8, the garment may include a blanket 800 (e.g., a compression blanket, a shroud, a cloak, an overcoat, a coat, a jacket, a scarf, and/or the like). The blanket 800 may include an open bottom so that a wearer's feet can still be operational. Alternatively, the blanket may completely enshroud a wearer.

Figure 9:
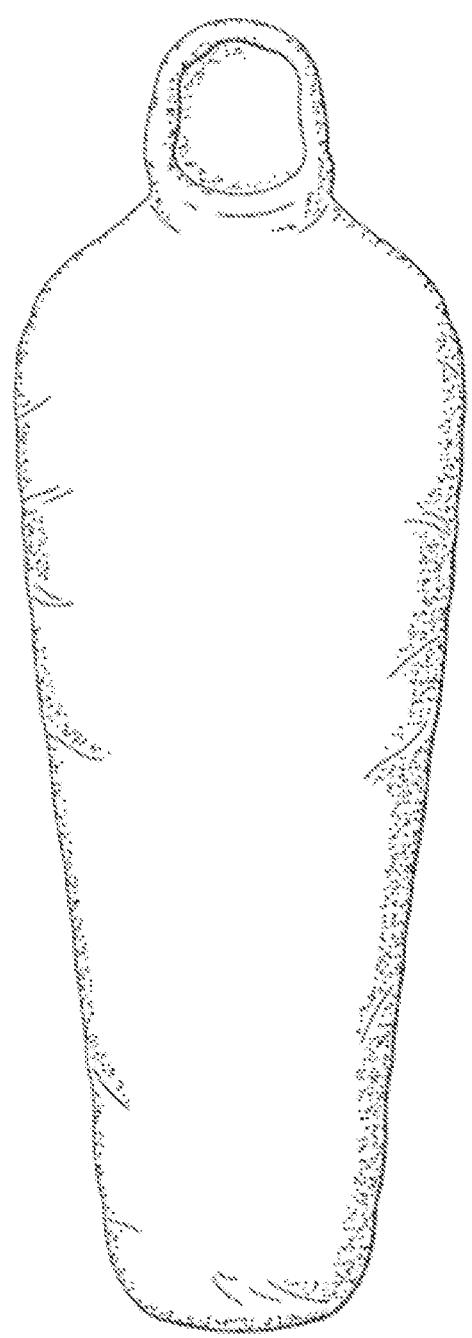
FIG. 9 illustrates an exemplary perspective view of a sleeping bag according to the present disclosure.

As seen in FIG. 9, the garment may include a sleeping bag 900 (e.g., a compression sleeping bag, a cocoon, and/or the like). The sleeping bag 900 may include a closed bottom so as to completely enshroud a wearer.

Figure 10:
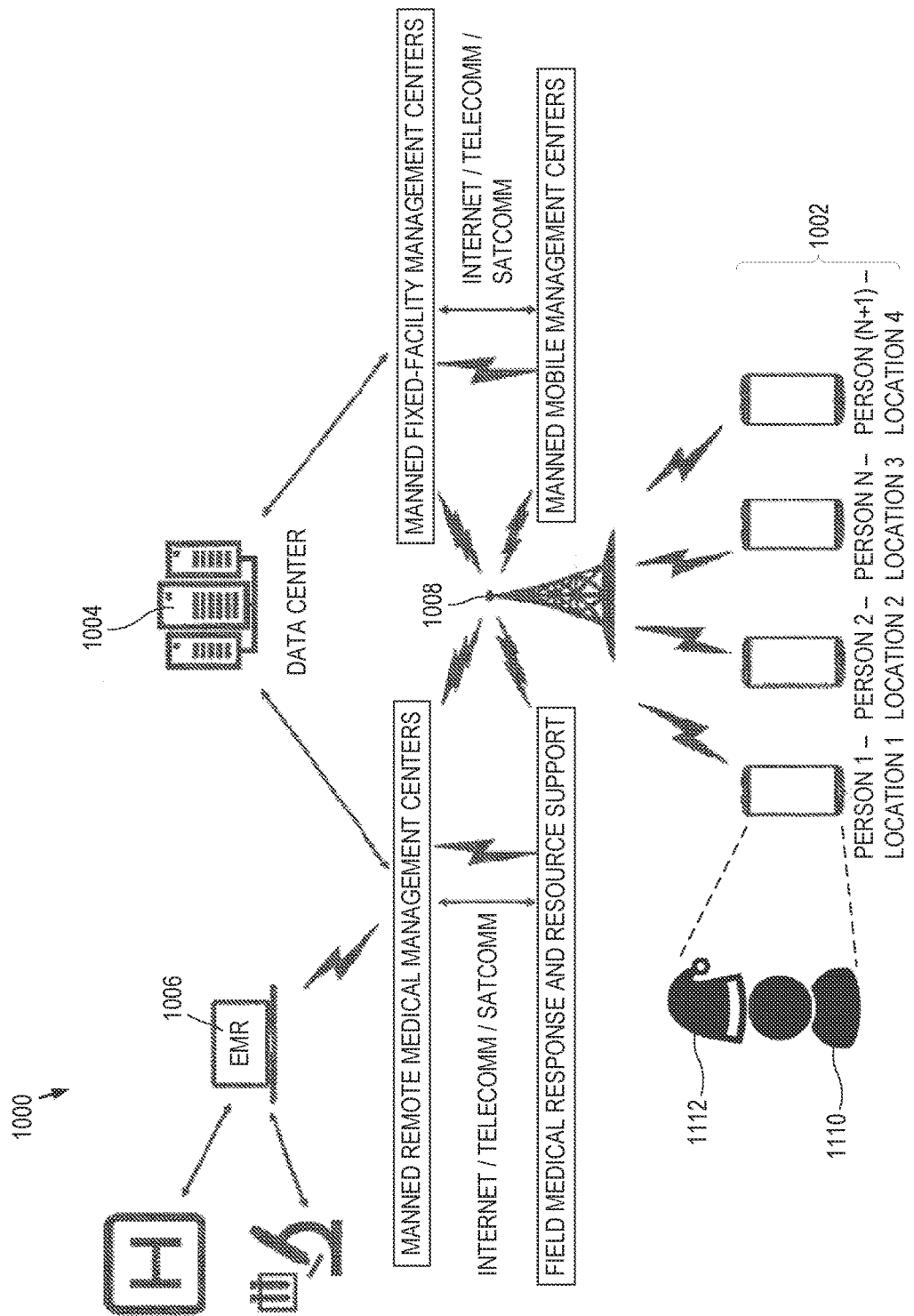
FIG. 10 illustrates an exemplary computing system according to the present disclosure.

FIG. 10 illustrates a computing system 1000 for enabling operation of the garments described herein. In some embodiments, the computing system 1000 may include a user device 1002, a data center 1004, and a management center 1006. Each of the user device 1002, the data center 1004, and the management center 1006, as well as any other element of the computing system 1000, may be communicatively coupled with one another via a network 1008 as described herein. As such, a variety of data may be transmitted between the user device 1002, the data center 1004, and the management center 1006 during operations described herein.

The user device 1002 may be associated with a user 1010 of a garment 1012 as described herein. For example, the user device 1002 may include the facemask 200, the gloves 202, and/or the boots 204 of FIG. 2, the full-body ensemble 300 of FIG. 3, the arm sleeve 400 of FIG. 4, the leg sleeve 500 of FIG. 5, the shoulder support 600 of FIG. 6, the hip support 700 of FIG. 7, the blanket 800 of FIG. 8, the sleeping bag 900 of FIG. 9, and/or any other garment disclosed herein. In some embodiments, the user device 1002 may include hardware such as a sensor, an accelerometer, a monitor, a probe, an actuator, a thermometer, a valve, a port, a sealant, a computer chip, a handheld computing device, a smart phone, a smart watch, a wearable device, a touch screen, a biometric device, a computing device, and/or any element of the computing environment 1100 described with reference to FIG. 11 and FIG. 12. Additionally, the user device 1002 may include multiple user devices configured to communicate with one another. For example, the user device 1002 may include a garment with multiple sensors as well as a smart phone for enabling the user to control operation of the garment.

The data center 1004 may be associated with a central computing device for processing data associated with users (e.g., the user 1010) and/or garments (e.g., garment 1012). For example, the data center 1004 may serve as a central repository for storing and/or processing collected garment data and/or user data that can later be accessed by various users. The data center 1004 may include a cloud-based server, mainframe server, a content server, a communication server, a laptop computer, a desktop computer, a handheld computing device, and/or any element of a computing environment as described herein (e.g., computing environment 1100 of FIG. 11 and FIG. 12). The data center 1004 may also include multiple computing devices configured to communicate with one another.

The management center 1006 may be associated with a computing device for remotely accessing data associated with users (e.g., the user 1010), ambient environments, and/or garments (e.g., garment 1012). For example, the management center 1006 may be associated with a computing device at a hospital, a science research laboratory, an emergency dispatch center, an information technology (IT) administration provider, and/or another third party facility that is used for accessing and/or processing collected data associated with users and/or garments. The management center 1006 may include a laptop computer, a desktop computer, a handheld computing device, a smart phone, a smart watch, a wearable device, a touchscreen, and/or any element of a computing environment as described herein (e.g., computing environment 1100 of FIG. 11 and FIG. 12). The management center 1006 may also include multiple computing devices configured to communicate with one another.

The network 1008 may include any wireless and/or wired communications network that facilitates communication between the user device 1002, the data center 1004, and/or the management center 1006, as well as between any other computing device (e.g., a third party server). For example, the network 1008 may include an Ethernet network, a cellular network, a computer network, the Internet, a wireless fidelity (Wi-Fi) network, a light fidelity (Li-Fi) network, a Bluetooth network, a radio frequency identification (RFID) network, a near-field communication (NFC) network, a laser-based network, and/or the like. In some embodiments, the network 1008 may also include a plurality of networks.

Figure 11:
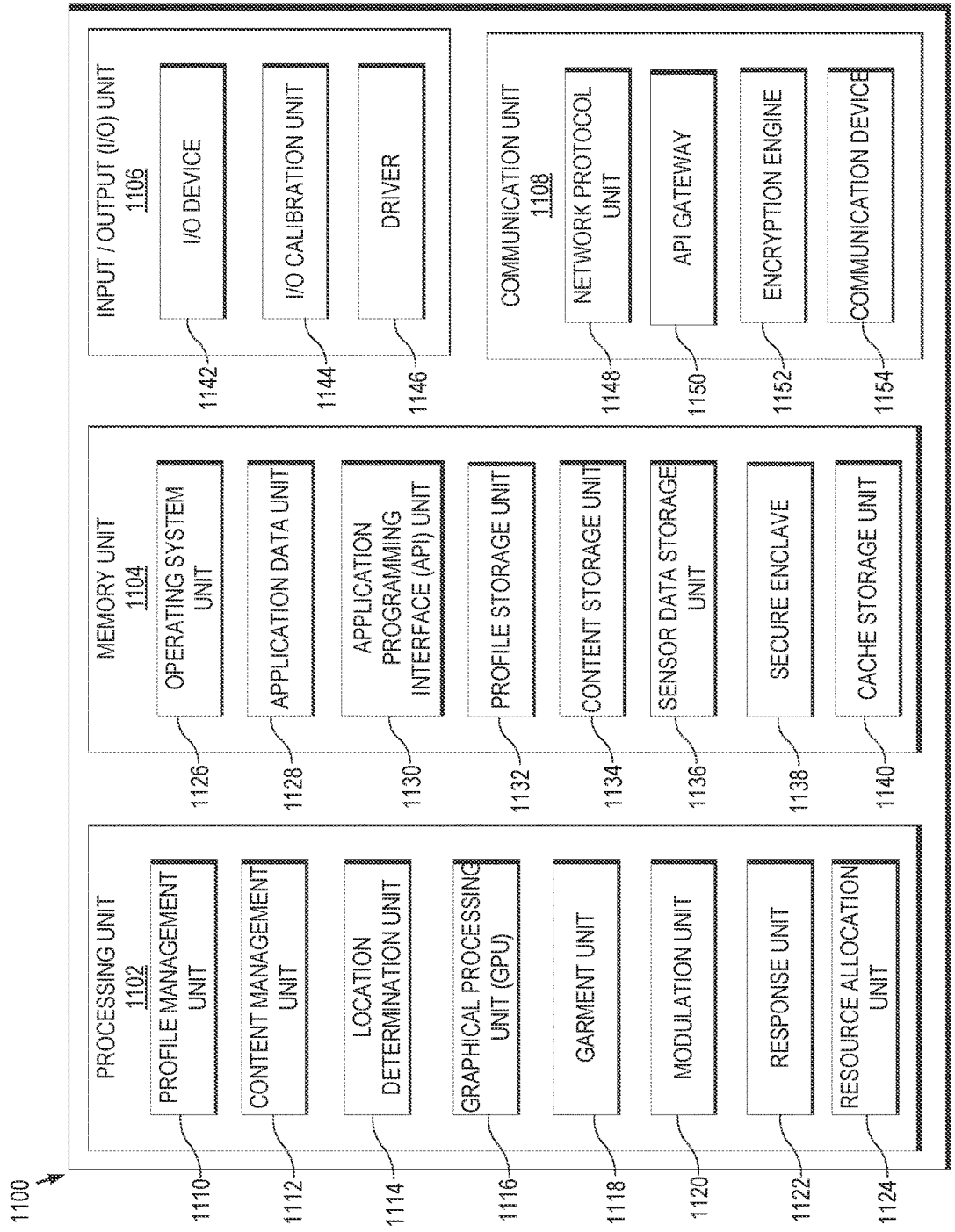
FIG. 11 illustrates an exemplary computing environment according to the present disclosure.
Figure 12:
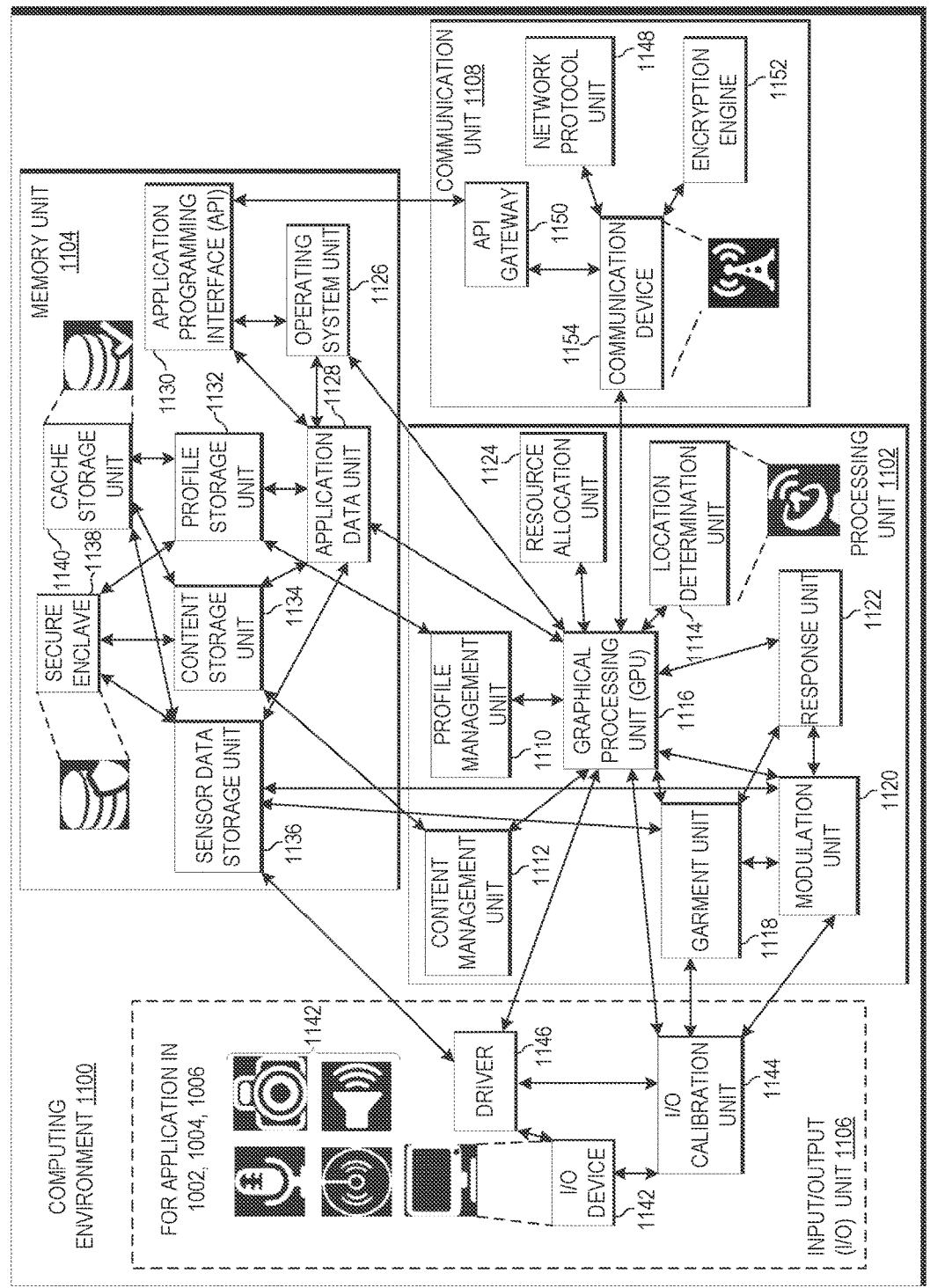
FIG. 12 illustrates an exemplary connectivity diagram of the computing environment of FIG. 11.

FIG. 11 and FIG. 12 illustrate exemplary functional and system diagrams of a computing environment 1100 for operation of the intelligent garments described herein. Specifically, FIG. 11 provides a functional block diagram of the computing environment 1100, whereas FIG. 12 provides a detailed system diagram of the computing environment 1100. Additionally, any units and/or subunits described herein with reference to the computing environment 1100 of FIG. 11 and/or FIG. 12 may be included in one or more elements of FIG. 10 such as the user device 1002, the data center 1004, and/or the management center 1006. The computing environment 1100 and/or any of its units and/or subunits described herein may include general hardware, specifically-purposed hardware, and/or software.

The computing environment 1100 may include, among other elements, a processing unit 1102, a memory unit 1104, an input/output (I/O) unit 1106, and/or a communication unit 1108. As described herein, each of the processing unit 1102, the memory unit 1104, the I/O unit 1106, and/or the communication unit 1108 may include and/or refer to a plurality of respective units, subunits, and/or elements. Furthermore, each of the processing unit 1102, the memory unit 1104, the I/O unit 1106, and/or the communication unit 1108 may be operatively and/or otherwise communicatively coupled with each other so as to facilitate the operation of garments as described herein. Further, the processing unit 1102, the memory unit 1104, the I/O unit 1106, and/or the communication unit 1108 may refer to and/or be included in any of the user device 1002, the data center 1004, and/or the management center 1006 of FIG. 10.

The processing unit 1102 may control any of the one or more units 1104, 1106, 1108, as well as any included subunits, elements, components, devices, and/or functions performed by the units 1104, 1106, 1108 included in the computing environment 1100. The described sub-elements of the computing environment 1100 may also be included in similar fashion in any of the other units and/or devices included in the system 1000 of FIG. 10. Additionally, any actions described herein as being performed by a processor may be taken by the processing unit 1102 alone and/or by the processing unit 1102 in conjunction with one or more additional processors, units, subunits, elements, components, devices, and/or the like. Additionally, while only one processing unit 1102 may be shown in FIG. 11 and/or FIG. 12, multiple processing units may be present and/or otherwise included in the computing environment 1100 or elsewhere in the overall system (e.g., system 1000 of FIG. 10). Thus, while instructions may be described as being executed by the processing unit 1102 (and/or various subunits of the processing unit 1102), the instructions may be executed simultaneously, serially, and/or otherwise by one or multiple processing units.

In some embodiments, the processing unit 1102 may be implemented as one or more computer processing unit (CPU) chips and/or graphical processing unit (GPU) chips and may include a hardware device capable of executing computer instructions. The processing unit 1102 may execute instructions, codes, computer programs, and/or scripts. The instructions, codes, computer programs, and/or scripts may be received from and/or stored in the memory unit 1104, the I/O unit 1106, the communication unit 1108, subunits and/or elements of the aforementioned units, other devices and/or computing environments, and/or the like.

In some embodiments, the processing unit 1102 may include, among other elements, subunits such as a profile management unit 1110, a content management unit 1112, a location determination unit 1114, a graphical processing unit (GPU) 1116, a garment unit 1118, a modulation unit 1120, a response unit 1122, and/or a resource allocation unit 1124. Each of the aforementioned subunits of the processing unit 1102 may be communicatively and/or otherwise operably coupled with each other.

The profile management unit 1110 may facilitate generation, modification, analysis, transmission, and/or presentation of a profile associated with a garment and/or a user (e.g., wearer) of a garment. For example, the profile management unit 1110 may operate a database associated with a user and may manage information associated with garments worn by the user as described herein. The profile management unit 1110 may receive, process, analyze, organize, and/or otherwise transform any data received from the user and/or another computing element so as to generate a profile of a user and/or a garment that includes personal information (e.g., an age, a weight, a height), vitals (e.g., a resting heart rate, a core body temperature), contact information (e.g., an address, an email address, a phone number), garment information (e.g., a model name, a model number, an amount of fluid adsorbed in each layer), device information (e.g., a model number, a device type, operating system information), and/or location information (e.g., an Internet protocol (IP) address, global positioning system (GPS) coordinates) of the same.

The content management unit 1112 may facilitate generation, modification, analysis, transmission, and/or presentation of user interfaces for controlling operation of garments and/or processing data as described herein. For example, the content management unit 1112 may control the audio-visual environment and/or appearance of application data during execution of various processes. Media content for which the content management unit 1112 may be responsible may include advertisements, images, text, themes, audio files, video files, documents, and/or the like. In some embodiments, the content management unit 1112 may also interface with a third-party content server and/or memory location.

The location determination unit 1114 may facilitate detection, generation, modification, analysis, transmission, and/or presentation of location information. Location information may include global positioning system (GPS) coordinates, a mile marker, an Internet protocol (IP) address, a media access control (MAC) address, geolocation information, an address, a port number, a zip code, a server number, a proxy name and/or number, device information (e.g., a serial number), and/or the like. In some embodiments, the location determination unit 1114 may include various sensors, a radar, and/or other specifically-purposed hardware elements for enabling the location determination unit 1114 to acquire, measure, and/or otherwise transform location information into a useable format.

The GPU unit 1116 may facilitate generation, modification, analysis, processing, transmission, and/or presentation of data. In some embodiments, the GPU unit 1116 may be utilized to render visual content for presentation on a computing device. to analyze collected data, and/or the like. The GPU unit 1116 may also include multiple GPUs and therefore may be configured to perform and/or execute multiple processes in parallel.

The garment unit 1118 may facilitate operation of one or more sensors embedded in garments. For example, the garment unit 1118 may be utilized locally in a garment for enabling a sensor array network in the garment to receive and/or transmit various signals. For example, the garment unit 1118 may monitor user vitals, detect environmental conditions, and/or the like. In some embodiments, the garment unit 1118 may include GPUs and/or other processing elements so as to enable efficient operation of garments in either series or parallel. The garment unit 1118 may utilize a variety of I/O devices described herein for operating garments such as sensors, actuators, valves, pumps, dispensers, powered ingested, embedded, wearable, printed-flexible-and-organic-electronics (PFOEs), simplex-linked and networked linked sensors coupled with interfaced microprocessor programmable logical controllers, Arduino boards, and/or the like.

The modulation unit 1120 may facilitate the accurate real time processing of data collected by the garment unit 1118 so that any modulations (e.g., adjustments) to the garment may be made in response to detected environmental conditions, user vitals, and/or desired performance. The modulation unit 1120 may receive and/or transmit signals from the garment unit 1118 so that the user may obtain a desired performance of the garment. For example, upon determining that the user is in an extremely cold environment based on an analysis of collected sensor data, the modulation unit 1120 may transmit instructions to the garment unit 1118 for increasing an amount of reflection toward the body to maintain and/or raise the user's core body temperature.

The response unit 1122 may facilitate the post-processing of collected sensor data amongst medical dispatchers, researchers, and/or other users. The response unit 1122 may generate alerts or recommendations for medical assistance of a user, generate reports during research and development phases of new garments and/or garment technologies, and/or the like.

The resource allocation unit 1124 may facilitate the determination, monitoring, analysis, and/or allocation of computing resources throughout the garments and/or computing systems described herein. For example, the computing system 1000 of FIG. 10 may facilitate a high volume of (e.g., multiple) communication connections between a large number of supported garments and/or devices (e.g., the user device 1002, the data center 1004, and/or the management center 1006). As such, computing resources of the computing environment 1100 (and/or any subunit of the aforementioned units) such as processing power, data storage space, network bandwidth, and/or the like may be in high demand at various times during operation. Accordingly, the resource allocation unit 1124 may be configured to manage the allocation of various computing resources as they are required by particular units and/or subunits of the computing environment 1100 and/or other computing environments. In some embodiments, the resource allocation unit 1124 may include sensors and/or other specially-purposed hardware for monitoring performance of each unit and/or subunit of the computing environment 1100, as well as hardware for responding to the computing resource needs of each unit and/or subunit. In some embodiments, the resource allocation unit 1124 may utilize computing resources of a second computing environment separate and distinct from the computing environment 1100 to facilitate a desired operation.

For example, the resource allocation unit 1124 may determine a number of simultaneous communication connections and/or incoming requests for data and/or image processing. The resource allocation unit 1124 may then determine that the number of simultaneous communication connections and/or incoming requests for meets and/or exceeds a predetermined threshold value. Based on this determination, the resource allocation unit 1124 may determine an amount of additional computing resources (e.g., processing power, storage space of a particular non-transitory computer-readable memory medium, network bandwidth, and/or the like) required by the processing unit 1102, the memory unit 1104, the I/O unit 1106, the communication unit 1108, and/or any subunit of the aforementioned units for enabling safe and efficient operation of the computing environment 1100 while supporting the number of simultaneous communication connections and/or incoming requests. The resource allocation unit 1124 may then retrieve, transmit, control, allocate, and/or otherwise distribute determined amount(s) of computing resources to each element (e.g., unit and/or subunit) of the computing environment 1100 and/or another computing environment.

In some embodiments, factors affecting the allocation of computing resources by the resource allocation unit 1124 may include the number of ongoing communication connections and/or other communication channel connections, a number of garments and/or devices on a network, a duration of time during which computing resources are required by one or more elements of the computing environment 1100, and/or the like. In some embodiments, computing resources may be allocated to and/or distributed amongst a plurality of second computing environments included in the computing environment 1100 based on one or more factors mentioned above. In some embodiments, the allocation of computing resources of the resource allocation unit 1124 may include the resource allocation unit 1124 flipping a switch, adjusting processing power, adjusting memory size, partitioning a memory element, transmitting data, controlling one or more input and/or output devices, modifying various communication protocols, and/or the like. In some embodiments, the resource allocation unit 1124 may facilitate utilization of parallel processing techniques such as dedicating a plurality of GPUs included in the processing unit 1102.

In some embodiments, the memory unit 1104 may be utilized for storing, recalling, receiving, transmitting, and/or accessing various files and/or information during operation of the computing environment 1100. For example, the memory unit 1104 may be utilized for storing user profile information, garment information, sensor data, generated reports, and/or the like. The memory unit 1104 may include various types of data storage media such as solid state storage media, hard disk storage media, and/or the like. The memory unit 1104 may include dedicated hardware elements such as hard drives and/or servers, as well as software elements such as cloud-based storage drives. For example, the memory unit 1104 may include various subunits such as an operating system unit 1126, an application data unit 1128, an application programming interface (API) unit 1130, a profile storage unit 1132, a content storage unit 1134, a sensor data storage unit 1136, a secure enclave 1138, and/or a cache storage unit 1140.

The memory unit 1104 and/or any of its subunits described herein may include random access memory (RAM), read only memory (ROM), and/or various forms of secondary storage. RAM may be used to store volatile data and/or to store instructions that may be executed by the processing unit 1102. For example, the data stored may be a command, a current operating state of the computing environment 1100, an intended operating state of the computing environment 1100, and/or the like. As a further example, data stored in the memory unit 1104 may include instructions related to various methods and/or functionalities described herein. ROM may be a non-volatile memory device that may have a smaller memory capacity than the memory capacity of a secondary storage. ROM may be used to store instructions and/or data that may be read during execution of computer instructions. In some embodiments, access to both RAM and ROM may be faster than access to secondary storage. Secondary storage may be comprised of one or more disk drives and/or tape drives and may be used for non-volatile storage of data or as an over-flow data storage device if RAM is not large enough to hold all working data. Secondary storage may be used to store programs that may be loaded into RAM when such programs are selected for execution. In some embodiments, the memory unit 1104 may include one or more databases for storing any data described herein. Additionally or alternatively, one or more secondary databases located remotely from the computing environment 1100 may be utilized and/or accessed by the memory unit 1104.

The operating system unit 1126 may facilitate deployment, storage, access, execution, and/or utilization of an operating system utilized by the computing environment 1100 and/or any other computing environment described herein. In some embodiments, the operating system may include various hardware and/or software elements that serve as a structural framework for enabling the processing unit 1102 to execute various processing operations described herein. The operating system unit 1126 may further store various pieces of information and/or data associated with operation of the operating system and/or the computing environment 1100 as a whole, such as a status of computing resources (e.g., processing power, memory availability, resource utilization, and/or the like), runtime information, modules to direct execution of operations described herein, and/or the like.

The application data unit 1128 may facilitate deployment, storage, access, execution, and/or utilization of an application utilized by the computing environment 1100 and/or any other computing environment described herein (e.g., the user device 1002, the data center 1004, and/or the management center 1006 of FIG. 10). For example, users may be required to download, access, and/or otherwise utilize a software application on a computing device in order for various operations described herein to be performed. As such, the application data unit 1128 may store any information and/or data associated with the application. Information included in the application data unit 1128 may enable a user and/or computer processor to execute various operations described herein. The application data unit 1128 may further store various pieces of information and/or data associated with operation of the application and/or the computing environment 1100 as a whole, such as a status of computing resources (e.g., processing power, memory availability, resource utilization, and/or the like), runtime information, modules to direct execution of operations described herein, and/or the like.

The API unit 300 may facilitate deployment, storage, access, execution, and/or utilization of information associated with APIs of the computing environment 1100 and/or any other computing environment described herein. For example, the computing environment 1100 may include one or more APIs for enabling various devices, applications, and/or computing environments to communicate with each other and/or utilize common data. Accordingly, the API unit 1130 may include API databases containing information that may be accessed and/or utilized by applications and/or operating systems of other devices and/or computing environments. In some embodiments, each API database may be associated with a customized physical circuit included in the memory unit 1104 and/or the API unit 1130. Additionally, each API database may be public and/or private, and so authentication credentials may be required to access information via an API database.

The profile storage unit 1132 may facilitate deployment, storage, access, and/or utilization of information associated with profiles of users and/or garments. For example, the profile storage unit 1132 may store a user profile, identification information, vitals, garment information, location information, and/or metadata associated with a user and/or garment. In some embodiments, the profile storage unit 1132 may communicate with the profile management unit 1110 to receive and/or transmit information associated with a user and/or a garment.

The content storage unit 1134 may facilitate deployment, storage, access, and/or utilization of information associated with requested content by the computing environment 1100 and/or any other computing environment described herein. For example, the content storage unit 1134 may store one or more user interfaces, application information, and/or metadata to be presented to a user and/or otherwise utilized during operations described herein. In some embodiments, the content storage unit 1134 may communicate with the content management unit 1112 to receive and/or transmit content files.

The sensor data storage unit 1136 may facilitate deployment, storage, access, analysis, and/or utilization of information associated with users and/or garments as it is collected during operation of the garments. For example, the sensor data storage unit 1136 may store a user's vitals, muscle activity information, blood pressure information, external environmental information, fluid viscosity information, and/or the like. In some embodiments, the sensor data storage unit 1136 may communicate with the GPUs 1116, the garment unit 1118, the modulation unit 1120, and/or the response unit 1122 to facilitate analysis of any stored image frame and/or associated information.

The secure enclave 1138 may facilitate secure storage of data. In some embodiments, the secure enclave 1138 may include a partitioned portion of storage media included in the memory unit 1104 that is protected by various security measures. For example, the secure enclave 1138 may be hardware secured. In other embodiments, the secure enclave 1138 may include one or more firewalls, encryption mechanisms, and/or other security-based protocols. Authentication credentials of a user may be required prior to providing the user access to data stored within the secure enclave 1138.

The cache storage unit 1140 may facilitate short-term deployment, storage, access, analysis, and/or utilization of data. In some embodiments, the cache storage unit 1140 may serve as a short-term storage location for data so that the data stored in the cache storage unit 1140 may be accessed quickly. In some embodiments, the cache storage unit 1140 may include RAM and/or other storage media types that enable quick recall of stored data. The cache storage unit 1140 may include a partitioned portion of storage media included in the memory unit 1104.

The I/O unit 1106 may include hardware and/or software elements for enabling the computing environment 1100 to receive, transmit, and/or present information. For example, elements of the I/O unit 1106 may be used to capture sensor data associated with a user, an environment, and/or a garment, receive user input from a user via a user device, present information to a user, and/or the like. In this manner, the I/O unit 1106 may enable the computing environment 1100 to interface with a human user of the garment. As described herein, the I/O unit 1106 may include subunits such as an I/O device 1142, an I/O calibration unit 1144, and/or video driver 1146.

The I/O device 1142 may facilitate the receipt, transmission, processing, presentation, display, input, and/or output of information as a result of executed processes described herein. In some embodiments, the I/O device 1142 may include a plurality of I/O devices. For example, the I/O device 1142 may include a variety of elements that enable capturing of sensor data such as a sensor, a camera, a probe, a thermometer, a microphone, a valve, a pump, and/or the like. The I/O device 1142 may also include hardware for interfacing with a user, such as a display, a keyboard, a touchscreen, a button, a sensor, a biometric scanner, a laser, a microphone, a camera, and/or another element for receiving and/or collecting input from a user. Additionally and/or alternatively, the I/O device 1142 may include a display, a screen, a sensor, a vibration mechanism, a light emitting diode (LED), a speaker, a radio frequency identification (RFID) scanner, and/or another element for presenting and/or otherwise outputting data to a user. In some embodiments, the I/O device 1142 may communicate with one or more elements of the processing unit 1102 and/or the memory unit 1104 to execute operations described herein.

The I/O calibration unit 1144 may facilitate the calibration of the I/O device 1142. For example, the I/O calibration unit 1144 may detect and/or determine one or more settings of the I/O device 1142, and then adjust and/or modify settings so that the I/O device 1142 may operate more efficiently.

In some embodiments, the I/O calibration unit 1144 may utilize a driver 1146 (or multiple drivers) to calibrate the I/O device 1142. For example, a sensor driver 1146 may enable sensors included in a garment to be adequately calibrated in response to various instructions. In some embodiments, the I/O device 1142 may be calibrated by the I/O calibration unit 1144 by based on information included in the driver 1146.

The communication unit 1108 may facilitate establishment, maintenance, monitoring, and/or termination of communications (e.g., a communication connection) between computing devices of the intelligent garment system described herein. The communication unit 1108 may further enable communication between various elements (e.g., units and/or subunits) of the computing environment 1100. In some embodiments, the communication unit 1108 may include a network protocol unit 1148, an API gateway 1150, an encryption engine 1152, and/or a communication device 1154. The communication unit 1108 may include hardware and/or software elements.

The network protocol unit 1148 may facilitate establishment, maintenance, and/or termination of a communication connection between computing environment 1100 and another computing environment (e.g., the user device 1002, the data center 1004, and/or the management center 1006 of FIG. 10) by way of a network. For example, the network protocol unit 1148 may detect and/or define a communication protocol required by a particular network and/or network type. Communication protocols utilized by the network protocol unit 1148 may include Wi-Fi protocols, Li-Fi protocols, cellular data network protocols, Bluetooth® protocols, WiMAX protocols, Ethernet protocols, powerline communication (PLC) protocols, and/or the like. In some embodiments, facilitation of communication between the computing environment 1100 and any other device, as well as any element internal to the computing environment 1100, may include transforming and/or translating data from being compatible with a first communication protocol to being compatible with a second communication protocol. In some embodiments, the network protocol unit 1148 may determine and/or monitor an amount of data traffic to consequently determine which particular network protocol is to be used for establishing a video communication connection, transmitting data, and/or performing other operations described herein.

The API gateway 1150 may facilitate the enablement of other devices and/or computing environments to access the API unit 1130 of the memory unit 1104 of the computing environment 1100. For example, a user device may access the API unit 1130 via the API gateway 1150. In some embodiments, the API gateway 1150 may be required to validate user credentials associated with a user of a user device prior to providing access to the API unit 1130 to the user. The API gateway 1150 may include instructions for enabling the computing environment 1100 to communicate and share information with another device.

The encryption engine 1152 may facilitate translation, encryption, encoding, decryption, and/or decoding of information received, transmitted, and/or stored by the computing environment 1100. Using the encryption engine, each transmission of data may be encrypted, encoded, and/or translated for security reasons, and any received data may be encrypted, encoded, and/or translated prior to its processing and/or storage. In some embodiments, the encryption engine 1152 may generate an encryption key, an encoding key, a translation key, and/or the like, which may be transmitted along with any data content.

The communication device 1154 may include a variety of hardware and/or software specifically purposed to enable communication between the computing environment 1100 and another device, as well as communication between elements of the computing environment 1100. In some embodiments, the communication device 1154 may include one or more radio transceivers, chips, analog front end (AFE) units, antennas, processing units, memory, other logic, and/or other components to implement communication protocols (wired or wireless) and related functionality for facilitating communication between the computing environment 1100 and any other device. Additionally and/or alternatively, the communication device 1154 may include a modem, a modem bank, an Ethernet device such as a router or switch, a universal serial bus (USB) interface device, a serial interface, a token ring device, a fiber distributed data interface (FDDI) device, a wireless local area network (WLAN) device and/or device component, a radio transceiver device such as code division multiple access (CDMA) device, a global system for mobile communications (GSM) radio transceiver device, a universal mobile telecommunications system (UMTS) radio transceiver device, a long term evolution (LTE) radio transceiver device, a worldwide interoperability for microwave access (WiMAX) device, a GPS communications link, a radiofrequency transponder for networked communications by one or more modes of authorized, allocated FCC and ITU radiofrequency band plans transmission (ELF through THF) such as US FCC Part 97 Amateur Radio Operators Digital and Voice Mode Frequencies or US FCC Part 13 Commercial Radio Operators Digital and Voice Mode Frequencies, a laser to permit remote telemetry to and from the garment wearer within the wearers' ambient conditions and to other commercial or non-commercial networked devices for analysis and intelligence-gathering of performance, safety, capability and ongoing necessary adaptations, (e.g., human thermal balance management Internet-of-things devices) and/or another device used for communication purposes.

While various implementations in accordance with the disclosed principles have been described above, it should be understood that they have been presented by way of example only, and are not limiting. Thus, the breadth and scope of the implementations should not be limited by any of the above-described exemplary implementations, but should be defined only in accordance with the claims and their equivalents issuing from this disclosure. Furthermore, the above advantages and features are provided in described implementations, but shall not limit the application of such issued claims to processes and structures accomplishing any or all of the above advantages.

Various terms used herein have special meanings within the present technical field. Whether a particular term should be construed as such a "term of art," depends on the context in which that term is used. "Connected to," "in communication with," "communicably linked to," "in communicable range of" or other similar terms should generally be construed broadly to include situations both where communications and connections are direct between referenced elements or through one or more intermediaries between the referenced elements, including through the Internet or some other communicating network. "Network," "system," "environment," and other similar terms generally refer to networked computing systems that embody one or more aspects of the present disclosure. These and other terms are to be construed in light of the context in which they are used in the present disclosure and as those terms would be understood by one of ordinary skill in the art would understand those terms in the disclosed context. The above definitions are not exclusive of other meanings that might be imparted to those terms based on the disclosed context.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the implementations set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any implementations in this disclosure. Neither is the "Summary" to be considered as a characterization of the implementations set forth in issued claims. Furthermore, any reference in this disclosure to "implementation" in the singular should not be used to argue that there is only a single point of novelty in this disclosure. Multiple implementations may be set forth according to the limitations of the multiple claims issuing from this disclosure, and such claims accordingly define the implementations, and their equivalents, that are protected thereby. In all instances, the scope of such claims shall be considered on their own merits in light of this disclosure, but should not be constrained by the headings herein. Any words following the terms "including," "include," "for example" or any similar phrase shall be construed as illustrative and shall not limit the generality of preceding words.

Lastly, although similar reference numbers may be used to refer to similar elements for convenience, it can be appreciated that each of the various example implementations may be considered distinct variations.

What is claimed is:

1. A garment, comprising:
   a basal layer including a hydrophilic material and substantially saturated with an aqueous mixture, the basal layer being configured to contact a skin surface of a wearer to provide conductive heat transfer from the skin surface of the wearer to the aqueous mixture and to maintain contact of the aqueous mixture with the skin surface of the wearer over a treatment time while the garment is worn;
   a permeable spacer layer disposed on and in direct contact with an outer surface of the basal layer, the spacer layer being configured to pass vapor from the aqueous mixture toward an ambient environment and to provide a conductive barrier to limit transfer of heat from the ambient environment to the skin surface of the wearer:
   a reflective layer disposed on an outer surface of the spacer layer, wherein the reflective layer is configured to modulate the thermal permeability of the garment; and
   a hydrophobic layer disposed on an outer surface of the reflective layer.

2. The garment of claim 1, wherein the aqueous mixture includes water and at least one of ethanol, propanol, and isopropanol.

3. The garment of claim 1, wherein at least approximately 5% of the aqueous mixture by volume is alcohol.

4. The garment of claim 3, wherein no more than approximately 50% of the aqueous mixture by volume is the alcohol.

5. The garment of claim 1, wherein the basal layer is configured to absorb the aqueous mixture by at least one of surface fiber adsorption, core fiber imbibition, soaking, wetting, submersion, and electrostatic deposition.

6. The garment of claim 1, further comprising a sensor disposed between the basal layer and the hydrophobic layer and configured to collect data associated with at least one of the wearer, the garment, one or more garment layers, and the ambient environment.

7. The garment of claim 6, further comprising a garment unit configured to control operation of the garment in response to the data collected by the sensor.

8. The garment of claim 6, further comprising a transmitter configured to transmit the data collected by the sensor to a data center.

9. A system, comprising:
the garment of claim 6;
a data center configured to receive and store data collected from the sensor; and
a management center configured to process the data received at the data center.

10. The system of claim 9, further comprising a user device associated with the wearer of the garment and configured to display the data collected by the sensor.

11. The system of claim 9, wherein the management center is configured to determine, based on processing the data collected by the sensor, at least one of: an adjustment to be made to the garment a product enhancement to be made to the garment, and a medical service to be provided to the wearer.

12. The system of claim 9, wherein the management center is associated with at least one of a research laboratory, a medical services provider, an emergency response dispatcher, and the wearer of the garment.

13. The system of claim 9, wherein the garment includes at least one of a facemask, a hood, a hat, a balaclava, a toboggan, gloves, mittens, boots, socks, shoes, sandals, a full-body ensemble, a jumpsuit, a skeleton suit, a flight suit, an arm sleeve, a compression sleeve, an orthopedic or orthotic sleeve, an elbow sleeve, an upper arm sleeve, a forearm sleeve, a wrist sleeve, a leg sleeve, a knee sleeve, a thigh sleeve, a shin sleeve, an ankle sleeve, a shoulder sleeve, a shoulder support, a sling, a hip sleeve, a hip support, a blanket, a compression blanket, a shroud, a cloak, an overcoat, a coat, a jacket, a scarf, a sleeping bag, a compression sleeping bag, and a cocoon.

14. The garment of claim 6, wherein the sensor is configured to collect data associated with the wearer.

15. The garment of claim 14, wherein the data associated with the wearer is at least one of a weight, a height, a heart rate, a blood pressure, a core body temperature, a skin surface body temperature, a metabolic expenditure, and a movement of the wearer.

16. The garment of claim 6, wherein the sensor is configured to collect data associated with the ambient environment.

17. The garment of claim 16, wherein the data associated with the ambient environment is at least one of an air temperature, an air humidity, a wind speed, a dry bulb temperature, a wet-bulb temperature, an air pressure, an altitude, infrared irradiance, optical irradiance, and UV irradiance.

18. The garment of claim 1, wherein the spacer layer includes one or more vents.

19. The garment of claim 1, wherein the reflective layer includes one or more closable holes.

20. The garment of claim 1, wherein the hydrophobic layer includes one or more vents.

21. The garment of claim 1, wherein the garment includes at least one of a facemask, a hood, a hat, a balaclava, a toboggan, gloves, mittens, boots, socks, shoes, sandals, a full-body ensemble, a jumpsuit, a skeleton suit, a flight suit, an arm sleeve, a compression sleeve, an orthopedic or orthotic sleeve, an elbow sleeve, an upper arm sleeve, a forearm sleeve, a wrist sleeve, a leg sleeve, a knee sleeve, a thigh sleeve, a shin sleeve, an ankle sleeve, a shoulder sleeve, a shoulder support, a sling, a hip sleeve, a hip support, a blanket, a compression blanket, a shroud, a cloak, an overcoat, a coat, a jacket, a scarf, a sleeping bag, a compression sleeping bag, and a cocoon.

* * * * *